(12) United States Patent
Corpart et al.

(10) Patent No.: US 8,088,942 B2
(45) Date of Patent: Jan. 3, 2012

(54) PROCESS FOR SYNTHESIZING SELECTED ORGANIC PEROXIDES

(75) Inventors: Jean-Marc Corpart, Vourles (FR); Sandra Grimaldi, Sainte-Foy-les-Lyon (FR); Georges Martino-Gauchi, Lyons (FR); Philippe Maj, Brignais (FR)

(73) Assignee: Arkema France, Colombes (FR)

( * ) Notice: Subject to any disclaimer, the term of this patent is extended or adjusted under 35 U.S.C. 154(b) by 373 days.

(21) Appl. No.: 12/298,568

(22) PCT Filed: Apr. 27, 2007

(86) PCT No.: PCT/EP2007/054140
§ 371 (c)(1),
(2), (4) Date: Oct. 27, 2008

(87) PCT Pub. No.: WO2007/125091
PCT Pub. Date: Nov. 8, 2007

(65) Prior Publication Data
US 2009/0182162 A1   Jul. 16, 2009

Related U.S. Application Data

(60) Provisional application No. 60/815,423, filed on Jun. 21, 2006.

(30) Foreign Application Priority Data

Apr. 27, 2006   (EP) .................... 06300415

(51) Int. Cl.
   *C07C 69/96* (2006.01)
(52) U.S. Cl. ........................................ 558/264
(58) Field of Classification Search .......... 558/264
   See application file for complete search history.

(56) References Cited

U.S. PATENT DOCUMENTS

| 3,950,375 A | 4/1976 | McKee et al. |
| 4,075,236 A | 2/1978 | Wagle et al. |
| 4,999,402 A | 3/1991 | Yamamoto |
| 5,700,856 A | 12/1997 | Smith |
| 6,098,701 A | 8/2000 | Blomgren |
| 6,117,409 A | 9/2000 | Bertsch-Frank |
| 6,258,906 B1 | 7/2001 | Bodart |
| 6,433,208 B1 * | 8/2002 | Cozens ............... 558/264 |
| 6,617,408 B2 | 9/2003 | Bodart |
| 6,878,840 B2 | 4/2005 | Bodart |
| 7,087,693 B2 | 8/2006 | Tammer |
| 7,332,139 B2 | 2/2008 | Schette et al. |
| 2004/0109798 A1 | 6/2004 | Chopard et al. |
| 2004/0179983 A1 | 9/2004 | Balan |
| 2005/0119501 A1 | 6/2005 | Tammer |
| 2005/0131179 A1 | 6/2005 | Cozens |
| 2007/0053808 A1 | 3/2007 | Markowz et al. |
| 2009/0043122 A1 | 2/2009 | Azzawi |
| 2009/0076234 A1 | 3/2009 | Grimaldi |
| 2010/0022794 A1 | 1/2010 | Appel |
| 2010/0036152 A1 | 2/2010 | Appel |

FOREIGN PATENT DOCUMENTS

| DE | 10257239 | 1/2004 |
| FR | 2253760 | 7/1975 |
| GB | 1 055 985 | 1/1967 |
| GB | 1484675 | 9/1977 |
| WO | 2004096871 | 11/2004 |
| WO | 2005075419 | 8/2005 |

OTHER PUBLICATIONS

Novel Liquid Phase Microreactors for Safe Production of Hazardous Specialty Chemicals; Floyd,T.M. et al., Microreact. Technol. Ind. Prospects Proc. Int. Conf 3rd, pp. 171-180 (1999).
Organic Synthesis with Microstructured Reactors, Hessel, V. et al., Chem. Eng. Technol., 28, 3 pp. 267-284 (2005).
A Microfabricated Nanoreactor for Safe, Continous Generation and Use of Singlet Oxygen, Wootton, R.D.R., et al., Organic Process Researcg & Development, 6, 187-189 (2002).
Non-Final Office Action issued in co-pending U.S. Appl. No. 12/298,571 mailed on Aug. 2, 2010.
Amendment filed on Feb. 2, 2011, in co-pending U.S. Appl. No. 12/298,571.
Final Office Action issued in co-pending U.S. Appl. No. 12/298,571 mailed on Apr. 14, 2011.

* cited by examiner

*Primary Examiner* — Rei-tsang Shiao
(74) *Attorney, Agent, or Firm* — Kimberly R. Hild

(57) ABSTRACT

The present invention relates to a process for the continuous preparation of selected organic peroxides using plate exchangers having a high heat exchange capacity.

13 Claims, 1 Drawing Sheet

PROCESS FOR SYNTHESIZING SELECTED ORGANIC PEROXIDES

FIELD OF THE INVENTION

The present invention relates to the synthesis of thermally sensitive selected organic peroxides, and more particularly relates to a process for the continuous preparation of selected organic peroxides using plate exchangers.

BACKGROUND OF THE INVENTION

The below selected organic peroxides are unstable and thermally sensitive compounds, i.e. compounds that decompose under the effect of temperature, because of the presence of the oxygen-oxygen bond which can open within an energy range $\Delta H$ of from approximately 84 to 184 kJ/mol, depending on the nature of the organic peroxide.

Thermally sensitive organic compounds, such as the below selected organic peroxides according to the invention, result in the formation of radicals by thermal decomposition. Advantage is taken of this decomposition in order to use these compounds as free-radical reaction initiators, but it needs to be perfectly controlled during the manufacture of these compounds.

Thus, the synthesis of the below selected organic peroxides requires very important precautions in order to prevent any accident in the industrial processes used. Generally, open reactors are used, making it possible in this way to compensate for any runaway of the reaction without the product being contained, which would lead to irreparable damage (Encyclopaedia of Chemical Technology—Kirk-Othmer—Fourth Edition, Vol. 187, 1996, pages 292 to 293).

Moreover, in batch processes, all the reactants are initially loaded into the reactor, this type of process generally being used for the completely safe production of moderate amounts of compounds.

When greater production volumes are required, continuous processes are carried out. In continuous processes, the starting materials are continuously introduced into a reaction zone and kept in this zone for the required reaction period. The presence, at each moment, of a small amount of unstable compounds in the reaction mass makes continuous processes safer than batch processes, while at the same time providing greater productivity and higher purity for the products obtained.

Mention may, for example, be made of U.S. Pat. No. 4,075,236, which describes a process and a device for the continuous preparation of very pure peroxyesters with a high throughput. This process uses two open reaction zones in series comprising stirring devices which intimately mix the reactants, and cooling devices which dissipate the reaction heat. The cooled reaction mixture leaving the reactor is then continuously introduced into a separating device. The products are obtained with a yield of greater than 90% and have a purity of greater than 99%.

U.S. Pat. No. 3,950,375 describes a process for the continuous preparation of peroxydicarbonates, also using two stirred and cooled open reactors in series, the reaction product then being isolated by centrifugation. The products are obtained with a purity of greater than 99% and the productivities, expressed by parts by weight (kg) and per hour, are of the order of 50.

In these processes of the prior art, the reactors nevertheless contain a large volume of organic peroxide-based reaction mixture, which can lead to risks of a possible exothermic reaction such as a decomposition, despite the presence of a device for dissipating the reaction heat. Moreover, the mechanical stirrers conventionally used may not provide optimal mixing of the reaction phases, all the more so since these phases are generally immiscible.

These disadvantages of prior art are resolved by carrying out, according to the invention, the synthesis of the below selected organic peroxides using a closed plate exchanger running as micro-reactor or mini-reactor technology.

By using such technology, it is now possible to drastically reduce the reaction volume and to very precisely control the temperature of the reaction medium so as to satisfy the elementary criteria of safety, while at the same time improving the productivity of the plant. The quality of mixing is very important, since very rapid and very effective mixing of the reactants all along the reactor makes it possible to achieve very short periods of time spent by the reactants in the reactor and makes it possible to carry out reactions in a few seconds, even when the mixtures are two-phase mixtures. As a result, by use of micro-reactors or mini-reactors only small volumes of reaction mixture based on the below selected organic peroxides will limit the risks associated with a possible exothermic reaction such as a decomposition. Moreover, a good heat exchange, expressed as exchange surface relative to reaction volume, makes it possible to control and master more successfully the possible decomposition reactions of these compounds.

These essential advantages result in an improvement in the safety of the industrial processes for the synthesis of the below selected organic peroxides.

The micro-reactor or mini-reactor technology is based on a system of miniaturized reactors, of mixers, of heat exchangers and other elements with structures on a scale that can range from a micrometer to a millimeter.

To use a process in a closed reactor is one of the advantages of micro-reactor or mini-reactor technologies. Micro-reactors and mini-reactors can operate continuous by use of miniaturized tube reactors having small size channels. Moreover, because of the reduced size of the channels and thus high surface-to-volume ratios, they will be much more efficient than conventional batch reactors, in terms of mass and heat transfer. This technology is particularly suitable for the completely safe synthesis of the below selected dangerous organic peroxides of the invention.

The article entitled "Novel Liquid Phase Microreactors for Safe Production of Hazardous Specialty Chemicals" in Microreact. Technol. Ind. Prospects, Proc. Int. Conf. 3rd, 171-180 (1999), presents the advantage of microreactors in relation to the possibility of producing reactors with small channels that can be produced by microfabrication techniques. That article describes a microreactor which comprises two groups of five microchannels corresponding to elementary flow rates of the two reactants which are remixed in a tube online. The microreactor may comprise a heat exchange device and temperature detectors. A mixing time of 10 ms and a heat transfer coefficient of 1445 $W/m^{2\circ}$ C. are obtained and the reactor is shown to operate with 11 psi pressure drop at the 1.0 ml/min design flow rate. Such a microreactor presents the disadvantage of not enabling extrapolation to an industrial scale, the production volume for a single microreactor being only about 1000 lbs/yr. To expand the production capacity, it is necessary to scale out with a great number of microreactors used in parallel. This disadvantage is resolved by using, according to the present invention, a single microreactor with considerably higher flow that may consist of a large number of plates defining between them reaction chambers connected in series.

The publications Chem. Eng. Technol. 2005, 28, 3, pp. 276-284 and Organic Process Research & Development, 2002, 6, pp. 187-189 make reference to preparations, in a microstructured reactor, of cyclic peroxides such as ascaridole from α-terpinene and singlet oxygen generated by irradiation.

Document DE 10257239 describes the continuous photo-oxidation of olefins in microreactors, in the presence of light and oxygen, so as to prepare organic intermediates such as, for example, allyl hydroperoxides, 1,2-dioxetanes or endoperoxides. In this case, it is not a liquid-liquid reaction.

Application WO 04/091771 describes a microreactor that is particularly suitable for the preparation of hydrogen peroxide by reaction of hydrogen and oxygen. This microreactor is composed of plates and comprises a reaction zone included between the plates. These plates can optionally contain a catalyst and allow the reaction exothermicity to be dissipated. The spacing between the plates, called slot, is less than 1500 micrometers in size. Gas-phase heterogeneous reactions are advantageously carried out in these devices.

Document EP 1 313 554 relates to a process for carrying out reactions between at least two reactive fluids, using a reactor having spaces between two plates in the form of slots. The reactions carried out are exothermic or endothermic reactions between several reactants, in the presence or absence of catalyst. The process is particularly suitable for heterogeneous reactions in the presence of a granular catalyst placed either in the reaction spaces, or on the lateral surfaces of the wall elements which are turned towards the reaction spaces. This process is used for the direct synthesis of hydrogen peroxide in the gas phase, for the preparation of propenal or of acrylic acid from propene, or the production of ethylene oxide or of propylene oxide.

In addition, in WO 02/085511, a plate exchanger is disclosed for exchange and/or reaction between at least two fluids. Inlet nozzles may be considered to enable inlets of one or several reactants in the reaction chamber. Endothermic or exothermic reactions can be carried out in these plate exchangers. However, this document neither discloses nor suggests to use such an exchanger for a process for synthesis the below selected organic peroxides.

An industrial process suitable for the synthesis of the below selected organic peroxides using a close plate exchanger running as microreactor or minireactor technology, that limits their decomposition and that provides a high degree of industrial safety, with high yields and high degrees of purity, has now been discovered.

This process can be carried out advantageously as an ex-situ process, i.e. on the site where free-radical cross-linkings or polymerizations are carried out in the presence of an organic peroxide selected from the group consisting of di(n-propyl)peroxydicarbonate of CAS Reg. No. 16066-38-9, di(sec-butyl)peroxydicarbonate of CAS Reg. No. 19910-65-7, di(2-ethylhexyl)peroxydicarbonate of CAS Reg. No. 16111-62-9, 1,1-dimethyl-3-hydroxybutyl peroxyneodecanoate of CAS Reg. No. 95718-78-8, α-cumyl peroxyneodecanoate of CAS Reg. No. 26748-47-0, α-cumyl peroxyneoheptanoate of CAS Reg. No. 104852-44-0, tert-amyl peroxyneodecanoate of CAS Reg. No. 68299-16-1, tert-butyl peroxyneodecanoate of CAS Reg. No. 26748-41-4, tert-amyl peroxypivalate of CAS Reg. No. 29240-17-3, tert-butyl peroxypivalate of CAS Reg. No. 927-07-1, 2,5-dimethyl-2,5-di(2-ethylhexanoylperoxy)hexane of CAS Reg. No. 13052-09-0, tert-amyl peroxy-2-ethylhexanoate of CAS Reg. No. 686-31-7, tert-butyl peroxy-2-ethylhexanoate of CAS Reg. No. 3006-82-4, tert-amyl peroxyacetate of CAS Reg. No. 690-83-5, tert-butyl peroxyacetate of CAS Reg. No. 107-71-1, tert-amyl perbenzoate of CAS Reg. No. 4511-39-1, tert-butyl perbenzoate of CAS Reg. No. 614-45-9, OO-tert-amyl-O(2-ethylhexyl)monoperoxycarbonate of CAS Reg. No. 70833-40-8, OO-tert-butyl-O-isopropyl monoperoxy-carbonate of CAS Reg. No. 2372-21-6, OO-tert-butyl 1-(2-ethylhexyl) monoperoxy-carbonate of CAS Reg. No. 34443-12-4, poly (tert-butyl peroxycarbonate)polyether of CAS Reg. No. 100-41-4, decanoyl peroxide of CAS Reg. No. 762-12-9, lauroyl peroxide of CAS Reg. No. 105-74-8, succinic acid peroxide of CAS Reg. No. 123-23-9, benzoyl peroxide of CAS Reg. No. 94-36-0, 1,1-di(tert-butylperoxy)-3,3,5-trimethylcyclohexane of CAS Reg. No. 6731-36-8,1,1-di(tert-butylperoxy) cyclohexane of CAS Reg. No. 3006-86-8, 1,1-di(tert-amylperoxy)cyclohexane of CAS Reg. No. 15667-10-4, n-butyl 4,4-di(tert-butylperoxy)valerate of CAS Reg. No. 995-33-5, ethyl 3,3-di(tert-amylperoxy)butyrate of CAS Reg. No. 67567-23-1, tert-butyl peroctoate of CAS Reg. No. 3006-82-4, ethyl 3,3-di(tert-butylperoxy)butyrate of CAS Reg. No. 55794-20-2, cumene hydroperoxide of CAS Reg. No. 80-15-9, and tert-butyl hydroperoxide of CAS Reg. No. 75-91-2, said organic peroxide being used directly just after it has been produced in the polymerization or cross-linking reactor, more particularly introduced continuously in the course of the polymerization or cross-linking reaction.

DETAILED DESCRIPTION OF THE INVENTION

A subject of the present invention is a process for the continuous preparation of organic peroxides selected from the group consisting of di(n-propyl) peroxydicarbonate, di(sec-butyl)peroxy-dicarbonate, di(2-ethylhexyl)peroxydicarbonate, 1,1-dimethyl-3-hydroxybutyl peroxyneodecanoate, α-cumyl peroxyneodecanoate, α-cumyl peroxyneoheptanoate, tert-amyl peroxyneodecanoate, tert-butyl peroxyneodecanoate, tert-amyl peroxypivalate, tert-butyl peroxypivalate, 2,5-dimethyl-2,5-di(2-ethylhexanoylperoxy)hexane, tert-amyl peroxy-2-ethylhexanoate, tert-butyl peroxy-2-ethylhexanoate, tert-amyl peroxyacetate, tert-butyl peroxyacetate, tert-amyl perbenzoate, tert-butyl perbenzoate, OO-tert-amyl-O(2-ethylhexyl)monoperoxy-carbonate, OO-tert-butyl-O-isopropyl monoperoxy-carbonate, OO-tert-butyl 1-(2-ethylhexyl) monoperoxy-carbonate, poly(tert-butyl peroxycarbonate) polyether, decanoyl peroxide, lauroyl peroxide, succinic acid peroxide, benzoyl peroxide, 1,1-di (tert-butylperoxy)-3,3,5-trimethylcyclohexane, 1,1-di(tert-butylperoxy)-cyclo-hexane, 1,1-di(tert-amylperoxy)cyclohexane, n-butyl 4,4-di(tert-butylperoxy)valerate, ethyl 3,3-di (tert-amylperoxy)butyrate, tert-butyl peroctoate, ethyl 3,3-di (tert-butylperoxy)butyrate, cumene hydro-peroxide, and tert-butyl hydroperoxide, and mixtures thereof, comprising introducing a reaction flow into a closed plate exchanger comprising at least three plates in contact with one another defining chambers connected in series, adding through at least 2 inlet points reactants into the reaction flow, tempering the reaction flow to a temperature within the range of from 0 to 100° C., reacting the reactants with the reaction flow to form said organic peroxides.

In one embodiment, the reaction flow is introduced at a flow rate ranging from 0.1 l/h to 5000 l/h.

Preferably, in the process of the invention, the flow rates for introduction of the reactants vary from 0.1 l/h to 2000 l/h, in particular from 1 l/h to 2000 l/h.

Surprisingly, it has been found that increasing the flow rates for introduction of the reactants allows to obtain high conversion despite the lower contact time. This lower contact time results in safe production of the selected organic peroxides.

Preferably, the temperature of the reaction flow being within the range of from 5 to 60° C.

It has been found that higher temperature in the process according the invention is generally needed compared to batch process to obtain similar peroxide yield. Despite higher reaction temperatures, the process of the present invention operates safely.

In a continuous reactor, sections of liquid are successively entering progressively one behind the other without ever mixing. A tubular reactor is a most common technological of a continuous reactor. However, the conventional tubular reactor has a limited heat exchange coefficient. To obtain high productivities measured in l/h relative to the volume of the reactor, if the reactions are exothermic, then the reactor must have a high exchange capacity measured in terms of surface-to-volume ratio. As, furthermore, the above selected organic peroxides are thermally sensitive, it is necessary to limit the maximum temperature reached, and to introduce the reactants at several points along the process flow so as to control this maximum temperature.

The number of inlet points is determined such that the temperature in the reaction zone does not exceed a given value, which is generally the temperature above which the organic peroxide becomes thermally sensitive.

BRIEF DESCRIPTION OF THE DRAWINGS

Other characteristics and advantages of the invention will emerge more clearly on reading the description that follows and with reference to the attached figures in which.

Figure 1:
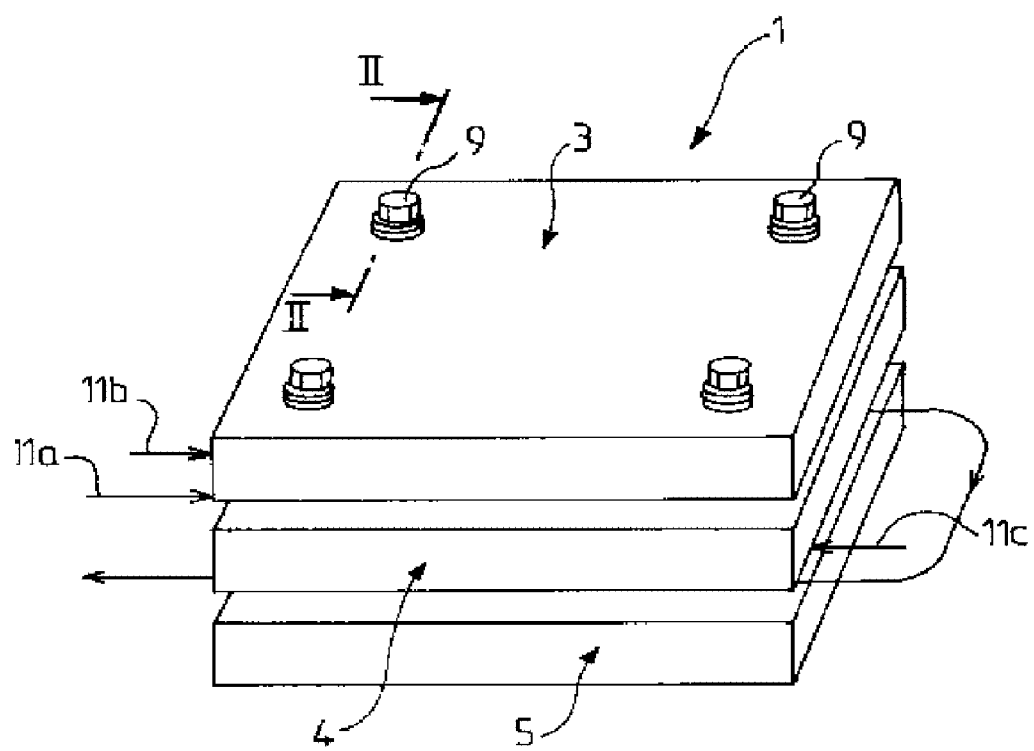
FIG. 1 represents diagrammatically an elevation of a plate exchanger that can be used in the process of the invention.

In the plate exchangers of the process according to the invention, makes it possible to reduce the reaction volume and to handle high exothermicities in the reaction zone. The reaction is carried out in small-sized channels, which improves the interfacial contact and decreases the reaction times. The disposal of the heat is facilitated by a high heat exchange capacity expressed as surface area relative to reaction volume.

Thus, in terms of advantages with respect to the reaction medium, in comparison with data derived from batch processes in conventional open reactors, for which the surface/volume ratios are of the order of a few $m^2/m^3$, and in particular for rapid and exothermic reactions, the process according to the invention gives better productivity, better conversion, better selectivity, a better yield and a better quality of the processes of the prior art. Side reactions are minimized, which facilitates the subsequent purification steps and thus reduces the waste to be treated and the manufacturing costs. From a safety point of view, it is possible to carry out reactions without risk, in higher temperature ranges than those conventionally used, which have the effect of accelerating the reaction rates and thus further improving the productivity of the processes.

In environmental terms, the fact that the preparation of unstable compounds is carried out in the closed exchangers of the process according to the invention will reduce volatile organic compound (VOC) emissions.

The continuous systems have other advantages in terms of flexibility, since it is possible to regulate the time spent in the system. In case of a continuous plate exchanger system the number of plates constituting the exchanger is another way of regulating the time spent in the system; the exchanger may consist of a large number of plates that are parallel with respect to one another.

The plate exchangers that may be suitable for the process of the invention are micro-reactors described in the state of the art, for example the systems described in document EP 1 313 554 mentioned above or in application WO 02/085511, the content of which is incorporated by way of reference.

The systems can also be improved by setting up devices for separating the plates in the event of a situation of reaction shift, such as an increase in pressure or in temperature resulting from a decomposition phenomenon. In the event of a positive pressure, the exchanger operating in closed mode then becomes an open reactor so as to allow the product to be evacuated and to manage the problem completely safely. These devices for separating the plates may consist of a system allowing the plates to move apart, in particular:

nut-bolt systems that deform plastically beyond a certain pressure, nut-bolt systems assembled with springs that compress if the pressure in the reactor exceeds a given value, nut-bolt systems assembled with elastic washers, of Belleville washer type, calculated such that the plates separate by a given distance if the pressure exceeds a defined value. This system also has the advantage of returning to its initial state as soon as the pressure has returned below the defined value.

The organic peroxides that can be prepared according to the process of the invention being selected from the group consisting of di(n-propyl)peroxydicarbonate of CAS Reg. No. 16066-38-9, di(sec-butyl)peroxydicarbonate of CAS Reg. No. 19910-65-7, di(2-ethylhexyl)peroxydicarbonate of CAS Reg. No. 16111-62-9, 1,1-dimethyl-3-hydroxybutyl peroxyneodecanoate of CAS Reg. No. 95718-78-8, α-cumyl peroxyneodecanoate of CAS Reg. No. 26748-47-0, α-cumyl peroxyneoheptanoate of CAS Reg. No. 104852-44-0, tert-amyl peroxyneodecanoate of CAS Reg. No. 68299-16-1, tert-butyl peroxyneodecanoate of CAS Reg. No. 26748-41-4, tert-amyl peroxypivalate of CAS Reg. No. 29240-17-3, tert-butyl peroxypivalate of CAS Reg. No. 927-07-1, 2,5-dimethyl-2, 5-di(2-ethylhexanoylperoxy)hexane of CAS Reg. No. 13052-09-0, tert-amyl peroxy-2-ethylhexanoate of CAS Reg. No. 686-31-7, tert-butyl peroxy-2-ethylhexanoate of CAS Reg. No. 3006-82-4, tert-amyl peroxyacetate of CAS Reg. No. 690-83-5, tert-butyl peroxyacetate of CAS Reg. No. 107-71-1, tert-amyl perbenzoate of CAS Reg. No. 4511-39-1, tert-butyl perbenzoate of CAS Reg. No. 614-45-9, OO-tert-amyl-O(2-ethylhexyl)monoperoxycarbonate of CAS Reg. No. 70833-40-8, OO-tert-butyl-O-isopropyl monoperoxy-carbonate of CAS Reg. No. 2372-21-6, OO-tert-butyl 1-(2-ethylhexyl) monoperoxycarbonate of CAS Reg. No. 34443-12-4, poly(tert-butyl peroxycarbonate)polyether of CAS Reg. No. 100-41-4, decanoyl peroxide of CAS Reg. No. 762-12-9, lauroyl peroxide of CAS Reg. No. 105-74-8, succinic acid peroxide of CAS Reg. No. 123-23-9, benzoyl peroxide of CAS Reg. No. 94-36-0, 1,1-di(tert-butylperoxy)-3, 3,5-trimethylcyclohexane of CAS Reg. No. 6731-36-8,1,1-di (tert-butylperoxy)cyclohexane of CAS Reg. No. 3006-86-8, 1,1-di(tert-amylperoxy)cyclohexane of CAS Reg. No. 15667-10-4, n-butyl 4,4-di(tert-butylperoxy)valerate of CAS Reg. No. 995-33-5, ethyl 3,3-di(tert-amylperoxy)butyrate of CAS Reg. No. 67567-23-1, tert-butyl peroctoate of CAS Reg. No. 3006-82-4, ethyl 3,3-di(tert-butylperoxy)butyrate of CAS Reg. No. 55794-20-2, cumene hydroperoxide of CAS Reg. No. 80-15-9, and tert-butyl hydroperoxide of CAS Reg. No. 75-91-2.

The reactions carried out so as to obtain organic peroxides selected from the group consisting of di(n-propyl) peroxydicarbonate of CAS Reg. No. 16066-38-9, di(sec-butyl)peroxy-dicarbonate of CAS Reg. No. 19910-65-7, di(2-ethylhexyl) peroxydicarbonate of CAS Reg. No. 16111-62-9, 1,1-dimethyl-3-hydroxybutyl peroxy-neodecanoate of CAS Reg. No. 95718-78-8, α-cumyl peroxyneodecanoate of CAS Reg. No. 26748-47-0, α-cumyl peroxyneoheptanoate of CAS Reg. No. 104852-44-0, tert-amyl peroxyneodecanoate of CAS Reg. No. 68299-16-1, tert-butyl peroxyneodecanoate of CAS Reg. No. 26748-41-4, tert-amyl peroxypivalate of CAS Reg. No. 29240-17-3, tert-butyl peroxypivalate of CAS Reg. No. 927-07-1, 2,5-dimethyl-2,5-di(2-ethylhexanoylperoxy)hexane of CAS Reg. No. 13052-09-0, tert-amyl peroxy-2-ethylhexanoate of CAS Reg. No. 686-31-7, tert-butyl peroxy-2-ethylhexanoate of CAS Reg. No. 3006-82-4, tert-amyl peroxyacetate of CAS Reg. No. 690-83-5, tert-butyl peroxyacetate of CAS Reg. No. 107-71-1, tert-amyl perbenzoate of CAS Reg. No. 4511-39-1, tert-butyl perbenzoate of CAS Reg. No. 614-45-9, OO-tert-amyl-O(2-ethylhexyl)monoperoxycarbonate of CAS Reg. No. 70833-40-8, OO-tert-butyl-O-isopropyl monoperoxycarbonate of CAS Reg. No. 2372-21-6, OO-tert-butyl 1-(2-ethylhexyl) monoperoxycarbonate of CAS Reg. No. 34443-12-4, poly(tert-butyl peroxycarbonate)polyether of CAS Reg. No. 100-41-4, decanoyl peroxide of CAS Reg. No. 762-12-9, lauroyl peroxide of CAS Reg. No. 105-74-8, succinic acid peroxide of CAS Reg. No. 123-23-9, benzoyl peroxide of CAS Reg. No. 94-36-0, 1,1-di(tert-butylperoxy)-3,3,5-trimethylcyclohexane of CAS Reg. No. 6731-36-8,1,1-di(tert-butylperoxy)cyclohexane of CAS Reg. No. 3006-86-8, 1,1-di(tert-amylperoxy)cyclohexane of CAS Reg. No. 15667-10-4, n-butyl 4,4-di(tert-butylperoxy)valerate of CAS Reg. No. 995-33-5, ethyl 3,3-di(tert-amylperoxy)butyrate of CAS Reg. No. 67567-23-1, tert-butyl peroctoate of CAS Reg. No. 3006-82-4, ethyl 3,3-di(tert-butylperoxy)butyrate of CAS Reg. No. 55794-20-2, cumene hydroperoxide of CAS Reg. No. 80-15-9, and tert-butyl hydroperoxide of CAS Reg. No. 75-91-2, according to the invention are most commonly liquid/liquid reactions. They can be carried out in the presence of catalysts. It is possible to prepare mixtures of chemical compounds according to the invention.

The reaction sequences resulting in the formation of the organic peroxides presented above are described in Encyclopaedia of Chemical Technology—Kirk-Othmer—Fourth Edition, Vol. 18, 1996, pages 230-310.

The simplified reaction sequences involved for obtaining the selected organic peroxides may be summarized as follows:

$$A+B \rightarrow I \qquad (1)$$

$$I+C \rightarrow X \qquad (2)$$

with A being a base or an acid, B and C being reactants, I an intermediate product and X the organic peroxide.

When A is a base, such as caustic soda or potassium hydroxide, an intermediate salt I is prepared by reaction with an alkyl hydroperoxide or hydrogen peroxide as reactant B. Then the salt I reacts with a chlorinated acylating agent as reactant C, such as an acid chloride or an alkyl chloroformate. Thus, peroxydicarbonates, peroxyesters and diacylperoxides above presented may be prepared according to this general sequence reaction.

Hydroperoxides and diperoxyketals above presented are generally prepared by acid-catalysed reaction. Hydroperoxides may be produced commercially by mixing either alcohol or olefin as reactant B with a strong acid as reactant A such as hydrochloric acid, sulfuric acid, para toluene sulfonic acid for example, followed by reaction (2) with hydrogen peroxide as reactant C. Diperoxyketals are generally obtained by reaction of a ketone as reactant B with two equivalents of an alkyl hydroperoxide as reactant C in the presence of an acid as reactant A.

Preferably, the reaction in the process of the invention is carried out in basic medium at a $pH \geq 9$ or in acidic medium at a $pH \leq 2$.

An additional advantage provided by the use of the closed plate exchangers of the process according to the invention, compared with existing technologies, is that of being able to prepare the above selected organic peroxides in the solid state using a reaction temperature that is above their melting point. Peroxide-based formulations such as peroxide micro-emulsions can also be prepared.

The reactants can be introduced by means of peristaltic pumps, metering pumps, self-priming transfer pumps or centrifugal pumps; preferably, metering pumps or pumps used in liquid chromatography (HPLC) are used on a laboratory scale, and centrifugal pumps are used on an industrial scale.

Thermocouples can be provided on the exchanger for measuring the temperature, and also pressure measuring devices.

The internal pressure of the exchanger can vary in the range of from 0 to 5 bar, relative to atmospheric pressure, but depends on the number of plates and on the introduction flow rates.

The amount of time spent in the system, can be within the range of from some seconds to a few minutes, typically from 1 second to 10 minutes, in particular from 1 to 45 seconds for the laboratory scale, and up to 2 to 3 minutes on an industrial scale.

The heat-transfer fluid may consist of water, of brine or of a water/alcohol mixture, and the temperature of the heat-transfer fluid can range from −20° C. to 90° C., and more particularly from 0 to 50° C.

The reaction mixture derived from the plate exchanger can be subjected to a subsequent separation/washing step if necessary, and is, in this case, sent into a continuous separation unit, for instance that described in Chemical Engineers' Handbook, R. H. Perry/C. H. Chilton, Vol. 21, pp. 11-12.

The process according to the invention may be used also for synthesizing organic peroxides selected from the group consisting of dialkyl peroxides and ketone peroxides.

The following examples illustrate the invention without, however, limiting the scope thereof.

Figure 2:
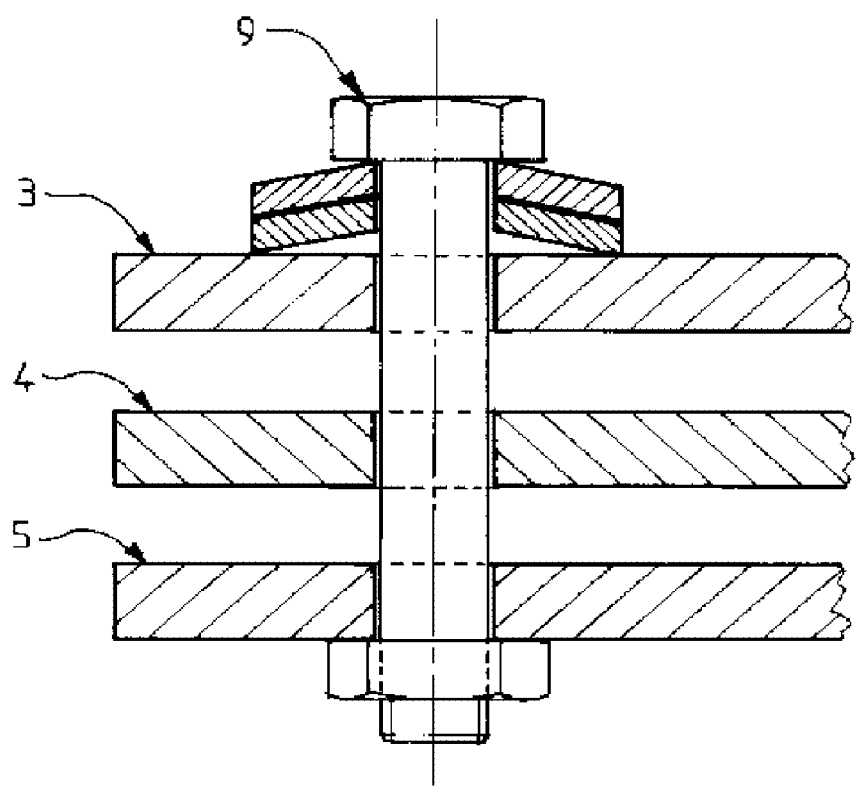
FIG. 2 represents diagrammatically a longitudinal section of the system of separation of the plates of the exchanger of FIG. 1.

Example of a Plate Exchanger that can be Used in the Process According to the Invention with Reference to FIGS. 1 and 2.

This exchanger 1 comprises 3 parallel plates 3,4,5, for the synthesis of above selected organic peroxides, and kept in contact with one another during the synthesis by means of nuts-bolts 9. This system 9, which is represented in detail in FIG. 2, can, in the event of an increase in pressure or in temperature, be opened so as to move the 2 plates apart and to ensure evacuation of the reactants completely safely. The use of micro-reactors allows, in the event of a leak or of incorrect operating, a reduced outlet of products, limiting the risk of accident or of explosion. This exchanger comprises several inlet points 11 for the reactants necessary for the manufacture of the above defined organic peroxides, in this case 3 in number. A cooling system (not represented in the figure) makes it possible to cool the system.

In the examples, the following abbreviations are used:
TBHP: tert-butyl hydroperoxide
PCl: pivaloyl chloride
C12: isododecane
CBO: benzoyl chloride
CL: lauroyl chloride
2-EHC: 2-ethyl hexanoyl chloride
2-EHCf: 2-ethyl hexyl chloroformate
TBA: tert-butyl alcohol

EXAMPLE 1

Preparation of 85% n-propyl Peroxydicarbonate in Isodecane (Known Commercially as Luperox© 221)

For this preparation, a plate exchanger as represented in FIG. 1, with a surface/volume ratio of 1800 m²/m³, comprising 3 inlet points 11 for the reactants, is used. Water cooled to 15° C., with a flow rate of 60 l/h, is used as utility for the cooling system (not represented in the figure).

5.5 l/h of a 7.8% NaOH sodium hydroxide solution are introduced continuously into the plate exchanger via point 11a, and 0.2 l/h of a 69.7% hydrogenperoxide $H_2O_2$ solution are introduced via point 11b. After the reaction which lasts approximately 6 seconds at 21° C., a mixture containing n-propylchloroformate and isodecane in proportions by mass of 88/12 is subsequently introduced continuously, via point 11c, at a flow rate of 1.2 l/h. The reaction is carried out at 21° C. A peroxide in solution in isodecane is obtained with a purity of 80% (corresponding to a purity of 96% of concentrated peroxide) and a yield of 63%, expressed relative to the chloroformate. The amount of n-propanol formed by hydrolysis in the aqueous phase is 1.45% relative to the amount of chloroformate.

In the following examples 2 to 14, a plate exchanger as represented in FIG. 1 has been used but more plates have been added. All the used plates are identical. The reactants A and B are always introduced continuously into the first plate of the plate exchanger via two different inlet points. Reactant C is introduced into the second plate of the plate exchanger. The temperature is measured in each plate.

After the reactor the products are fed into a settler where the watery phase is separated from the organic one. For each preparation, we have determined the conversion rate of reactant B or C and the peroxide yield recovered in the organic phase, expressed relatively to reactant C.

EXAMPLES 2 TO 3

Preparation of tert-butyl Peroxypivalate (Known Commercially as Luperox© 11)

| example | | 2 | 3 |
|---|---|---|---|
| Feed rate A | nature | KOH/H2O | KOH/H2O |
| | wt % | 23 | 23 |
| | l/h | 2.08 | 0.95 |
| Feed rate B | nature | TBHP/H2O | TBHP/H2O |
| | wt % | 69 | 69 |
| | l/h | 1.54 | 0.77 |
| Feed rate C | nature | PCl/C12 | PCl/C12 |
| | wt % | 70 | 70 |
| | l/h | 1.80 | 0.80 |
| Total feed | l/h | 5.42 | 2.52 |
| number of plates | | 5 | 5 |
| P1 | ° C. | 15 | 13 |
| P2 | ° C. | 22 | 22 |
| P3 | ° C. | 22 | 22 |
| P4 | ° C. | 22 | 22 |
| P5 | ° C. | 21 | 22 |
| Conversion C | % | 96% | 92% |
| Peroxide yield | % | 88% | 81% |
| By-product yield | % | 8% | 6% |

Surprisingly better results have been obtained in terms of conversion and yield when the reactant feed rate is increased in spite of the resulting decrease of the contact time. The peroxide yield and the conversion rate of the reactant C are higher when the reaction flow increases. In a comparative batch preparation carried out with an excess of reactant C at a temperature of 8° C., it has been obtained a yield of 93% for the peroxide and 7% for the by-product after one hour of reaction. This result can be compared to the yield obtained in the plate exchanger but the contact time is then only of a few minutes.

EXAMPLES 4 To 6

Preparation of tert-butyl Perbenzoate (Known Commercially as Luperox© P)

| example | | 4 | 5 | 6 |
|---|---|---|---|---|
| Feed rate A | nature | NaOH/H2O | NaOH/H2O | NaOH/H2O |
| | wt % | 14.5 | 14.5 | 14.5 |
| | l/h | 1.56 | 2.10 | 2.10 |
| Feed rate B | nature | TBHP/H2O | TBHP/H2O | TBHP/H2O |
| | wt % | 69 | 69 | 69 |
| | l/h | 0.54 | 0.72 | 1.01 |
| Feed rate C | nature | CBO | CBO | CBO |
| | wt % | 100 | 100 | 100 |
| | l/h | 0.48 | 0.63 | 0.73 |
| Total feed | l/h | 2.58 | 3.45 | 3.84 |
| number of plates | | 8 | 8 | 8 |
| P1 | ° C. | 22 | 22 | 24 |
| P2 | ° C. | 27 | 28 | 45 |
| P3 | ° C. | 26 | 27 | 44 |
| P4 | ° C. | 26 | 27 | 43 |
| P5 | ° C. | 26 | 27 | 43 |
| P6 | ° C. | 26 | 27 | 43 |
| P7 | ° C. | 26 | 27 | 42 |
| P8 | ° C. | 26 | 27 | 42 |
| Conversion C | % | 77% | 84% | 96% |
| Peroxide yield | % | 69% | 77% | 93% |
| By-product yield | % | 8% | 7% | 3% |

The peroxide yield and the conversion rate of the reactant C are higher when the reaction flow increases.

EXAMPLES 7 To 8

Preparation of tert-butyl peroxy-2-ethylhexanoate (Known Commercially as Luperox© 26)

| example | | 7 | 8 |
|---|---|---|---|
| Feed rate A | nature | KOH/H2O | KOH/H2O |
| | wt % | 15 | 15 |
| | l/h | 1.69 | 2.54 |
| Feed rate B | nature | TBHP/H2O | TBHP/H2O |
| | wt % | 69 | 69 |
| | l/h | 0.60 | 0.90 |
| Feed rate C | nature | 2-EHC | 2-EHC |
| | wt % | 98 | 98 |
| | l/h | 0.68 | 1.00 |
| Total feed | l/h | 2.97 | 4.44 |
| number of plates | | 8 | 8 |
| P1 | ° C. | 25 | 21 |
| P2 | ° C. | 39 | 48 |
| P3 | ° C. | 39 | 48 |
| P4 | ° C. | 39 | 48 |
| P5 | ° C. | 39 | 47 |
| P6 | ° C. | 39 | 48 |
| P7 | ° C. | 39 | 47 |
| P8 | ° C. | 23 | 18 |
| Conversion C | % | 56% | 63% |
| Peroxide yield | % | 47% | 54% |
| By-product yield | % | 9% | 9% |

EXAMPLE 9

Preparation of di(2-ethylhexyl)perdicarbonate (Known Commercially as Luperox© 223)

| example | | 9 |
|---|---|---|
| Feed rate A | nature | NaOH/H2O |
| | wt % | 8 |
| | l/h | 2.62 |
| Feed rate B | nature | H2O2/H2O |
| | wt % | 70 |
| | l/h | 0.19 |
| Feed rate C | nature | 2-EHCf |
| | wt % | 100 |
| | l/h | 0.99 |
| Total feed | l/h | 3.80 |
| number of plates | | 9 |
| P1 | ° C. | 22 |
| P2 | ° C. | 25 |
| P3 | ° C. | 25 |
| P4 | ° C. | 25 |
| P5 | ° C. | 25 |
| P6 | ° C. | 25 |
| P7 | ° C. | 25 |
| P8 | ° C. | 25 |
| P9 | ° C. | 25 |
| Conversion C | % | 26% |
| Peroxide yield | % | 26% |

EXAMPLES 10 TO 12

Preparation of tert-butyl Hydroperoxide di(2-ethylhexyl) (Known Commercially as Luperox© TBH70)

In these examples 10 to 12, the reaction is carried out in acidic medium, reactant A being sulfuric acid solution and reactant C is introduced into the third plate of the plate exchanger instead of the second plate.

| example | | 10 | 11 | 12 |
|---|---|---|---|---|
| Feed rate A | nature | H2SO4/H2O | H2SO4/H2O | H2SO4/H2O |
| | wt % | 78 | 78 | 78 |
| | l/h | 0.81 | 0.66 | 0.48 |
| Feed rate B | nature | TBA/H2O | TBA/H2O | TBA/H2O |
| | wt % | 90 | 90 | 90 |
| | l/h | 1.41 | 1.51 | 1.63 |
| Feed rate C | nature | H2O2/H2O | H2O2/H2O | H2O2/H2O |
| | wt % | 70 | 70 | 70 |
| | l/h | 0.78 | 0.81 | 0.90 |
| Total feed | l/h | 3.00 | 2.98 | 3.01 |
| number of plates | | 5 | 5 | 5 |
| P1 | ° C. | 23 | 25 | 23 |
| P2 | ° C. | 23 | 25 | 23 |
| P3 | ° C. | 63 | 63 | 64 |
| P4 | ° C. | 63 | 63 | 63 |
| P5 | ° C. | 29 | 29 | 29 |
| Peroxide yield | % | 68% | 66% | 67% |

Results close to the productivity in batch process have been obtained but higher temperature is needed.

EXAMPLE 13

Preparation of Lauroyl Peroxide (Known Commercially as Luperox© LP)

| example | | 13 |
|---|---|---|
| Feed rate A | Nature | NaOH/H2O |
| | wt % | 10 |
| | l/h | 1.9 |
| Feed rate B | Nature | H2O2/H2O |
| | wt % | 50 |
| | l/h | 0.29 |
| Feed rate C | Nature | CL |
| | wt % | 100 |
| | l/h | 0.72 |
| Total feed | l/h | 2.91 |
| number of plates | | 5 |
| P1 | ° C. | 20 |
| P2 | ° C. | 50 |
| P3 | ° C. | 50 |
| P4 | ° C. | 50 |
| P5 | ° C. | 50 |

The reaction mixture flowing out from the fifth plate is then dispersed in a large mixture of water/ice allowing the final product to solidify. After 10 minutes of continuously operating, 96 grams of lauroyl peroxide are obtained with a purity of 98.1% after washing and drying and a yield of 86%, expressed relative to lauroyl chloride.

EXAMPLE 14

Preparation of 1,1-di(tert-butylperoxy)-3,3,5-trimethylcyclohexane (Known Commercially as Luperox© 231)

A mixture of trimethyl cyclohexanone (3 kg) and a 70% tert-butyl hydroperoxide aqueous solution (3.76 kg) is prepared and the organic phase is separated. 0.1 l/h of a 70% sulfuric acid solution are introduced continuously into the first plate of a plate exchanger comprising 5 plates and 2.1 l/h of the said organic phase are introduced into the first plate via another inlet point. The temperature of the first plate is maintained at 5° C. with a cooling flow of a mixture water/ethanol. 0.3 l/h of a 70% sulfuric acid solution are subsequently introduced continuously into the second plate at 20° C. The reaction is carried out at 20° C. in the following plates. 1.38 kg/h of Luperox© 231 with a purity of 97% are obtained after washing the organic out flow with a 10% sodium hydroxide solution.

The invention claimed is:

1. Process for the continuous preparation of one or more organic peroxides selected from the group consisting of peroxydicarbonates, peroxyesters, diacylperoxides, hydroperoxides, diperoxyketals, dialkyl peroxides and ketone peroxides comprising introducing a reaction flow at a flow rate ranging from 0.1 l/h to 5000 l/h into a closed plate exchanger, adding through at least 2 inlet points reactants into the reaction flow, tempering the reaction flow to a temperature within the range of from about 0 to about 100° C., and reacting the reactants with the reaction flow to form said one or more organic peroxides, wherein the reaction flow and reactants are selected based on the one or more organic peroxides which are selected.

2. Process according to claim 1, wherein the temperature of the reaction flow is within the range of from about 5 to about 60° C.

3. Process according to claim 1, characterized in that the plate exchanger comprises at least 3 inlet points.

4. Process according to claim 1, wherein the process comprises releasing pressure when the pressure exceeds a given value allowing the plates of the plate exchanger to move apart by the aid of a separating device for separating the plates.

5. Process according to claim 4, characterized in that the said separating device is selected from nut-bolt systems that deform plastically beyond a certain pressure; nut-bolt systems assembled with springs that compress if the pressure in the reactor exceeds a given value; or nut-bolt systems assembled with elastic washers, of Belleville washer type, such that the plates separate by a given distance if the pressure exceeds a defined value.

6. Process according to claim 1, characterized in that the reactions carried out are liquid/liquid reactions.

7. Process according to claim 1, characterized in that the pressure in the exchanger varies in the range of from 0 to 5 bar.

8. Process according to claim 1, characterized in that the reaction is carried out in basic medium at a pH $\geq 9$ or in acidic medium at a pH $\leq 2$.

9. Process according to claim 1, characterized in that a reaction mixture derived from the plate exchanger containing the one or more organic peroxides is subjected to a subsequent separation/washing step in a continuous separation unit.

10. Process according to claim 1, wherein the closed plate exchanger has at least a first plate and one or more subsequent plates and the process comprises:
adding into the reaction flow one or more base reactants through a first inlet point at the first plate and a second reactant through a second inlet point at the first plate to form an intermediate salt, wherein the second reactant is an alkyl hydroperoxide or hydrogen peroxide,
adding into the reaction flow a chlorinated acylating agent reactant through a first inlet point at the one or more subsequent plates to react with the intermediate salt in the reaction flow to form said one or more organic peroxides.

11. Process according to claim 1, wherein the closed plate exchanger has at least a first plate and one or more subsequent plates and wherein the process comprises:
adding into the reaction flow one or more acid reactants through a first inlet point at the first plate and a second reactant through a second inlet point at the first plate, wherein the second reactant is an alcohol or olefin; and
adding into the reaction flow a hydrogen peroxide reactant through a first inlet point at the one or more subsequent plates to form said one or more organic peroxides.

12. Process according to claim 1, wherein the process comprises:
adding into the reaction flow, in the presence of an acid reactant, a ketone reactant and an alkyl hydroperoxide reactant to form said one or more organic peroxides.

13. Process according to claim 1, wherein the one or more organic peroxides are selected from the group consisting of di(n-propyl)peroxydicarbonate, di(sec-butyl)peroxy-dicarbonate, di(2-ethylhexyl)peroxydicarbonate, 1,1-dimethyl-3-hydroxybutyl peroxyneodecanoate, α-cumyl peroxyneodecanoate, α-cumyl peroxyneoheptanoate, tert-amyl peroxyneodecanoate, tert-butyl peroxyneodecanoate, tert-amyl peroxypivalate, tert-butyl peroxypivalate, 2,5-dimethyl-2,5-di(2-ethylhexanoylperoxy)hexane, tert-amyl peroxy-2-ethylhexanoate, tert-butyl peroxy-2-ethylhexanoate, tert-amyl peroxyacetate, tert-butyl peroxyacetate, tert-amyl perbenzoate, tert-butyl perbenzoate, OO-tert-amyl-O(2-ethylhexyl) monoperoxy-carbonate, OO-tert-butyl-O-isopropyl monoperoxy-carbonate, OO-tert-butyl 1-(2-ethylhexyl) monoperoxy-carbonate poly(tert-butyl peroxycarbonate) polyether, decanoyl peroxide, lauroyl peroxide, succinic acid peroxide, benzoyl peroxide, 1,1-di(tert-butylperoxy)-3,3,5-trimethylcyclohexane, 1,1-di(tert-butylperoxy)-cyclohexane, 1,1-di(tert-amylperoxy)cyclohexane, n-butyl 4,4-di(tert-butylperoxy)valerate, ethyl 3,3-di(tert-amylperoxy)butyrate, tert-butyl peroctoate, ethyl 3,3-di(tert-butylperoxy)butyrate, cumene hydro-peroxide, and tert-butyl hydroperoxide, and mixtures thereof.

* * * * *